(12) United States Patent
Vogt et al.

(10) Patent No.: US 9,314,288 B2
(45) Date of Patent: Apr. 19, 2016

(54) DISPENSING DEVICE FOR BONE CEMENT

(75) Inventors: Sebastian Vogt, Erfurt (DE); Hubert Buechner, Nuremberg (DE)

(73) Assignee: Heraeus Medical GmbH, Wehrheim (DE)

( * ) Notice: Subject to any disclaimer, the term of this patent is extended or adjusted under 35 U.S.C. 154(b) by 285 days.

(21) Appl. No.: 13/822,685

(22) PCT Filed: Sep. 21, 2011

(86) PCT No.: PCT/EP2011/004715
§ 371 (c)(1),
(2), (4) Date: Mar. 13, 2013

(87) PCT Pub. No.: WO2012/038073
PCT Pub. Date: Mar. 29, 2012

(65) Prior Publication Data
US 2013/0172896 A1    Jul. 4, 2013

(30) Foreign Application Priority Data

Sep. 22, 2010   (DE) .......................... 10 2010 046 058

(51) Int. Cl.
*A61B 17/88*     (2006.01)
*B05C 17/015*    (2006.01)
*B05C 17/005*    (2006.01)

(52) U.S. Cl.
CPC .......... *A61B 17/8802* (2013.01); *A61B 17/8822* (2013.01); *A61B 17/8825* (2013.01); *B05C 17/0052* (2013.01); *B05C 17/00596* (2013.01);
(Continued)

(58) Field of Classification Search
CPC ............. B05C 17/015; B05C 17/0054; A61B 17/8822; A61J 1/2027

USPC ...................................................... 222/81, 83
See application file for complete search history.

(56) References Cited

U.S. PATENT DOCUMENTS 1,920,165 A * 8/1933 Andvig ........................... 222/80
2,818,999 A   1/1958 Miller
(Continued)

FOREIGN PATENT DOCUMENTS

CN    1496762 A    5/2004
CN    2832755 Y    11/2006
(Continued)

OTHER PUBLICATIONS

International Preliminary Report on Patentability for PCT Application No. PCT/EP2011/004715 dated Mar. 26, 2013.
(Continued)

*Primary Examiner* — David Bates
(74) *Attorney, Agent, or Firm* — Norris McLaughlin & Marcus, P.A.

(57) ABSTRACT

A discharge device discharges the content of a container by applying a compressed gas. The device has a housing, at least one compressed gas container, an operating device for setting a gas flow from the compressed gas container and an opening means for opening the compressed gas container. The opening means is movable in relation to the compressed gas container, and the device has a holder for securing the container on the device. The holder is in operative connection with the opening means in such a way that securing the container on the holder brings about a movement of the opening means in relation to the compressed gas container that opens the compressed gas container.

26 Claims, 3 Drawing Sheets

Figure 1:
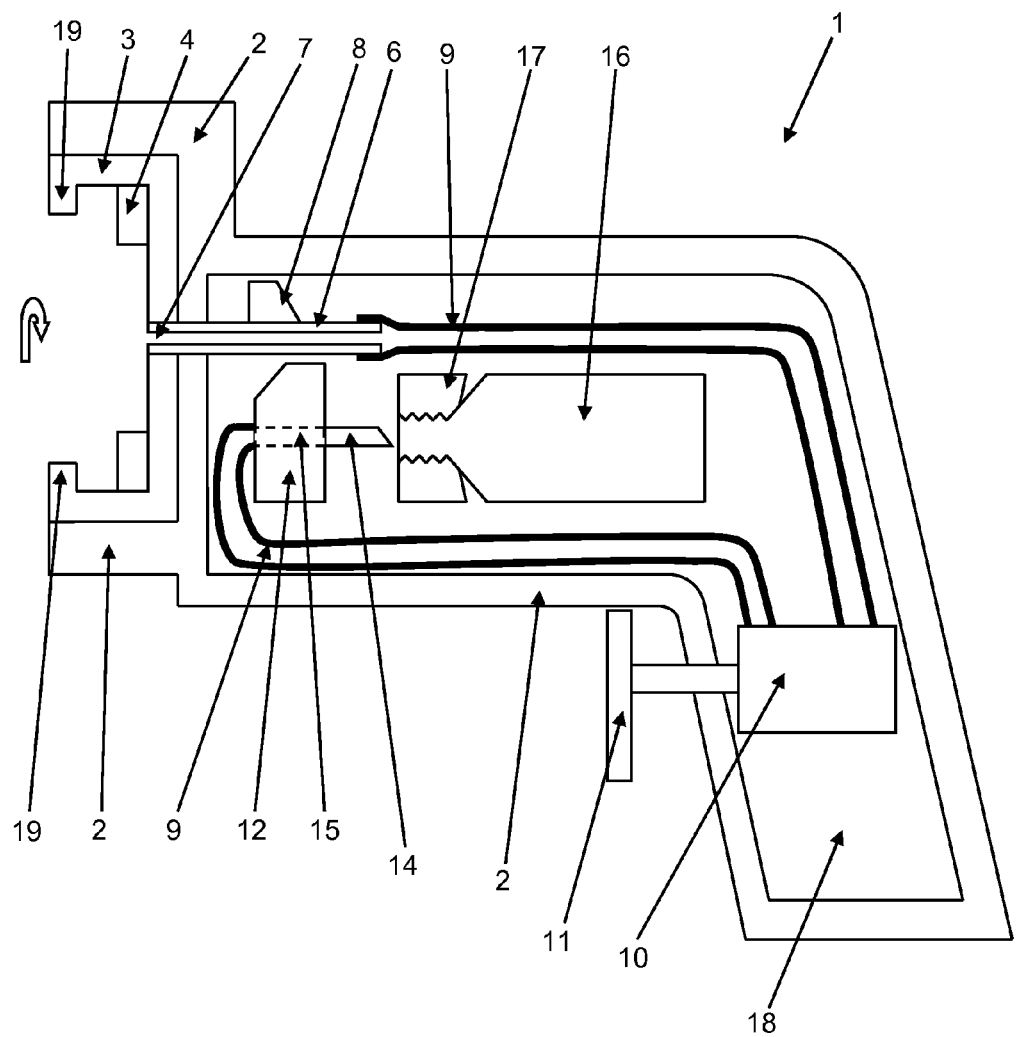

(52) U.S. Cl.
CPC ......... *B05C 17/015* (2013.01); *B05C 17/00553* (2013.01)

(56) References Cited

U.S. PATENT DOCUMENTS

| | | | |
|---|---|---|---|
| 3,568,892 | A | 3/1971 | Burk |
| 3,938,709 | A | 2/1976 | Collar |
| 4,475,664 | A * | 10/1984 | Mackal ............... 222/5 |
| 4,925,061 | A | 5/1990 | Jeromson, Jr. et al. |
| 5,004,127 | A * | 4/1991 | Morel ............... 222/521 |
| 5,076,468 | A * | 12/1991 | Mackal ............... 222/5 |
| 5,186,323 | A * | 2/1993 | Pfleger ............... 206/221 |
| 5,228,592 | A * | 7/1993 | Pellerano ............... 222/83 |
| 5,273,190 | A * | 12/1993 | Lund ............... 222/83 |
| 5,409,141 | A * | 4/1995 | Kikuchi et al. ............... 222/81 |
| 5,954,233 | A * | 9/1999 | Kawashima et al. ............ 222/83 |
| 6,089,403 | A * | 7/2000 | Mackal ............... 222/5 |
| 6,264,629 | B1 | 7/2001 | Landau |
| 6,422,412 | B1 * | 7/2002 | Sagawa ............... 220/277 |
| 6,478,771 | B1 * | 11/2002 | Lavi et al. ............... 604/82 |
| 6,589,087 | B2 * | 7/2003 | Mackal et al. ............... 441/93 |
| 6,935,541 | B1 | 8/2005 | Campbell et al. |
| 6,971,589 | B2 * | 12/2005 | Incardona et al. ............... 239/272 |
| 7,628,779 | B2 * | 12/2009 | Aneas ............... 604/411 |
| 8,051,884 | B2 * | 11/2011 | Reuter ............... 141/329 |
| 8,096,449 | B2 | 1/2012 | Keller |
| 8,226,126 | B2 * | 7/2012 | Johns et al. ............... 285/3 |
| 8,246,629 | B2 * | 8/2012 | Jonsson ............... 606/94 |
| 8,394,105 | B2 | 3/2013 | Vendrely et al. |
| 8,910,829 | B2 * | 12/2014 | Lazaris et al. ............... 222/5 |
| 2001/0008968 | A1 | 7/2001 | Overes et al. |
| 2003/0049981 | A1 | 3/2003 | Mackal et al. |
| 2004/0074927 | A1 | 4/2004 | Lafond |
| 2005/0230433 | A1 | 10/2005 | Campbell |
| 2005/0247740 | A1 | 11/2005 | Puzio |
| 2007/0181599 | A1 | 8/2007 | Kosmyna |
| 2007/0233147 | A1 | 10/2007 | Vendrely et al. |
| 2009/0302060 | A1 | 12/2009 | Keller |
| 2011/0272436 | A1 * | 11/2011 | Vogt et al. ............... 222/145.5 |
| 2011/0272437 | A1 * | 11/2011 | Vogt et al. ............... 222/389 |
| 2011/0272438 | A1 | 11/2011 | Vogt et al. |
| 2013/0172850 | A1 | 7/2013 | Vendrely et al. |
| 2014/0044805 | A1 * | 2/2014 | Kiss ............... 424/700 |
| 2014/0361036 | A1 * | 12/2014 | Brouillette et al. ............... 222/5 |

FOREIGN PATENT DOCUMENTS

| | | |
|---|---|---|
| EP | 0169533 A2 | 1/1986 |
| EP | 1118313 A1 | 7/2001 |
| EP | 1 118 313 B1 | 2/2005 |
| JP | 2007244868 A | 9/2007 |
| JP | 2009 543683 A | 12/2009 |
| JP | 2011 235962 A | 11/2011 |
| WO | 2008109439 A1 | 9/2008 |

OTHER PUBLICATIONS

International Search Report for PCT Application No. PCT/EP2011/004715 dated Jan. 17, 2012.
English-language Translation of Chinese Office Action for corresponding Chinese Application No. 201180045502.0 dated Jan. 28, 2015.
English translation of the Notice of Reasons for Rejection issued in corresponding Japanese Application No. 2013-529573 dated Mar. 18, 2014.
Patent Examination Report No. 1 issued Mar. 18, 2014 in corresponding Australia Application No. 2011304746.
English-language Translation of Chinese Office Action for corresponding Chinese Application No. 201180045502.0 dated Sep. 22, 2015.

* cited by examiner

DISPENSING DEVICE FOR BONE CEMENT

This is a 371 of PCT/EP2011/004715 filed 21 Sep. 2011 (international filing date), and claims the priority of German Application No. 10 2010 046 258.3 filed 22 Sep. 2010.

The invention relates to a dispensing device for extruding a content of a container through applying a compressed gas, comprising a housing, at least one compressed gas container, an operating facility for adjusting a gas flow from the compressed gas container, and opening means for opening the compressed gas container, whereby the opening means is mobile with respect to the compressed gas container.

The invention also relates to a method for activating a dispensing device, in which a container containing a material to be extruded is inserted into a bracket of the dispensing device, as well as a use of an extruding device according to the invention.

Accordingly, a compressed gas-operated extruding device for bone cements from cartridges or other containers is another object of the invention. In this context, the compressed gas is provided by a gas cartridge that is arranged in the extruding device. An extruding device is a dispensing device, in which the dispensing is effected through extruding from a container. Accordingly, the term, dispensing device, comprises extruding devices in the scope of the present invention as well.

It has been known for decades with regard to adhesives and sealants to extrude from cartridges or other containers by means of compressed gases.

U.S. Pat. No. 2,818,999 discloses a sealant gun that contains a gas cartridge in its handle. Once the cartridge is opened, the compressed gas from the gas cartridge presses a plunger within the cartridge towards the cartridge head. The flow of the pasty mass can be controlled through a central rod that extends through the cartridge and can close the outlet opening of the cartridge.

U.S. Pat. No. 3,938,709 describes a dispensing device, in which gas pressure is used to extrude from a tube that is situated inside the hollow gun body.

EP 0 169 533 A2 discloses an injection device for viscous substances. In this device, the process of extruding does not continue after the supply of compressed gas is interrupted, because an injection control valve interrupting the flow of viscous substance is situated at the outlet opening. The valve of the trigger grip can be used to control both the supply of gas and, simultaneously, the exit of the viscous substance. The injection control valve closes when no compressed gas is applied to it.

A similar system is described in U.S. Pat. No. 4,925,061. However, the injection control valve is actuated in this system through a rod that is connected to the trigger grip.

A gun for extruding bone cement is disclosed in EP 1 118 313 A1. The propulsion is effected through a gas cartridge in this case also. It is essential is that this very complex system includes a rod designed to expel the residual amount of cement contained in the dispensing tube. This elegant technical solution is well-suited for conventional polymethyl-methacrylate bone cements. However, said gun cannot be used for cartridge systems for mixing multiple components with a static mixer. Moreover, the manufacture of said gun is very elaborate.

US 2004/0074927 A1 describes an applicator gun has essentially the same features as the extruding gun disclosed in U.S. Pat. No. 4,925,061.

Printed publications US 2005/0230433 A1, US 2005/0247740 A1, and U.S. Pat. No. 6,935,541 B1 propose technical solution that are based on the inventive rationale of EP 0 169 533 A2.

WO 2008/109439 A1 discloses a generic compressed gas-operated dispensing device that uses a hydraulic medium onto which the compressed gas presses. The gas cartridge is opened through opening means having a hollow mandrel onto which the head of the gas cartridge is pressed while the gas cartridge is being screwed in.

The compressed gas is stored in a gas cartridge that is contained in the applicator in said devices. Conceivable gas cartridges are carbon dioxide cartridges of customary technology containing 8 g, 12 g or 16 g of carbon dioxide. Said cartridges are closed by means of metal seals. Said cartridges are easy to open by simple puncturing with a hollow mandrel.

It is a disadvantage of the above-mentioned dispensing devices propelled by means of gas cartridges that a user can empty said gas cartridge inadvertently as well before the cartridge or the container for the substance to be extruded is attached to the dispensing device. Accordingly, the user can inadvertently release the compressed gas without using it and without moving the substance to be extruded. Incorrect use is feasible as a result. In the worst case, the gas cartridge is already all empty before the cartridge of container for the material to be extruded is inserted. This is noticed, in the best of cases, during use and the gas cartridge then needs to be replaced at an inconvenient time. The time loss and laborious replacement can interfere significantly especially in scenarios in which dispensing devices of this type are used. Moreover, wasting gas cartridges produces costs and unnecessarily consumes resources.

Referring to said extruding devices being used in the operating theatre to apply bone cements, this may mean that the flow of the operation is disturbed since the bone cement cannot be extruded into the bone cavity after preparation of the implant bed. As a result, the surgery may take longer to complete and the attendant anaesthesia risk of the patient increases as well.

If the gas cartridge is opened already while the cartridge is not yet inserted properly, the cartridge may become detached due to the action of the compressed gas and move inadvertently through the operating theatre. A cartridge flying around can become a hazard for patients and OR staff alike.

Accordingly, it is the object of the invention to overcome the disadvantages of the prior art. In this context, a compressed gas-operated extruding device for cartridges or other containers, in particular for bone cements, is to be developed which is as safely as possible to handle and largely excludes the possibility of operating errors made by the user by means of design measures. Specifically, a dispensing device and a method for activating a dispensing device, in which inadvertent emptying and opening of the gas cartridge is prevented, are to be developed.

The object of the invention is met in that the dispensing device comprises a bracket for attaching the container to the dispensing device, whereby the bracket and the opening means are in operative connection such that attaching the container to the bracket results in a motion of the opening means with respect to the compressed gas container that opens the compressed gas container.

This ensures that the gas cartridge cannot be opened when the cartridge or the container is not yet connected to the dispensing device. In the scope of the invention, the term, container, comprises not only tubes and tubular bags but also cartridges and cartridge systems for bone cements, which are preferred containers in the scope of the present invention.

Adjusting a gas flow in the scope of the present invention means that the open cross-section of the conduit can be adjusted between at least two conduit cross-sections. Preferably, one of these is zero such that the gas flow is interrupted and/or the pressure from the compressed gas container is not transferred. Indeed, the way in which the pressure is transferred from the compressed gas container to the container is essential to the present invention. The gas pressure can be used to adjust the extrusion rate, i.e. the flow rate of the container content flowing out. Particularly preferably, the gas flow from the compressed gas container is continuously adjustable.

A dispensing device according to the invention can provide the compressed gas container to comprise at least one gas cartridge, in particular at least one $CO_2$ cartridge, whereby at least one of the gas cartridges can be opened through the opening means.

The invention can just as well provide the opening means to be shiftable in the longitudinal direction of the gas cartridge.

It is particularly advantageous for the invention to provide the container to be a cartridge or cartridge system having multiple cartridges, in particular arranged in parallel, whereby the cartridge or cartridge system preferably contains a bone cement, particularly preferably a multicomponent bone cement.

In this context, the invention can provide the cartridge or the cartridge system to have at least one feed plunger arranged in it that is mobile in it and can be driven by means of the gas pressure from the compressed gas container.

The feed plunger then expels the content of the cartridges from the cartridges. The feed plunger transfers the force acting through the gas pressure to the cartridge content.

Dispensing devices according to the invention can just as well be characterised in that the compressed gas container can be connected through at least one compressed gas conduit to an opening in the bracket, whereby the operating facility is arranged in the connection established through the compressed gas conduit or compressed gas conduits.

Conceivable compressed gas conduits in this context are suitably attached hoses as well as rigid tubes, bellows, and combinations thereof. In this context, the attachments of the compressed gas conduits are preferably connected to the connectors in a sufficiently firm manner such that the gas pressure does not detached from the compressed gas container.

In this context, the invention can provide the compressed gas conduit or compressed gas conduits to comprise at least one flexible section, in particular at least one piece of hose or bellows, or is or are made of at least one flexible hose or bellows.

A refinement of the invention provides the operating facility to comprise an adjustable throttle valve that can preferably be operated by means of a trigger.

Other operating facilities, such as a rotary button or a toggle, for operating the throttle valve are feasible just as well.

The invention can just as well provide the dispensing device to comprise a handle, preferably a gun handle, on which the trigger for operating the operating facility is preferably arranged.

In order to open suitable containers, the invention can provide the opening means to comprise a hollow mandrel that can be used to puncture, and thus open, the compressed gas container, whereby a pressure-tight connection to the compressed gas container can be established through the hollow mandrel and the hollow mandrel preferably is connected to the compressed gas conduit or compressed gas conduits.

In this context, the invention can provide the hollow mandrel to be flush on its outside with respect to the opening punctured into the compressed gas container.

According to a refinement, the invention provides the bracket to be arranged such as to be mobile with respect to the compressed gas container and the opening means to be connected fixedly to the bracket, whereby the container can be inserted into the bracket and the bracket comprises, for this purpose, snap-in locking means that engage opposite snap-in locking means on the container, and whereby the compressed gas container can be opened through the force acting on the bracket when the container is being attached in the bracket of the dispensing device.

In this context, the invention can provide that the compressed gas container can be or is connected fixedly to the housing and that the bracket having the opening means is arranged on the housing such as to be linearly mobile with respect to the housing.

This results in a dispensing device according to the invention having a shiftable bracket.

According to an alternative embodiment, the invention can provide that the container can be rotated or screwed into the bracket and the bracket to be arranged such that it can be rotated with respect to the opening means, whereby the bracket, in particular a tube on the bracket that extends into the inside of the housing, has a thread, which is interlocked with the opening means, arranged on it or a cam disk engaging a counter-part on the opening means arranged on it, and the opening means to be arranged such as to be linearly mobile with respect to the bracket and the compressed gas container such that a rotation of the bracket upon the container being attached to the bracket leads to a linear motion of the opening means with respect to the compressed gas container and thus to the compressed gas container being opened.

This results in a dispensing device according to the invention having a rotatable bracket.

In this context, the invention can provide that the compressed gas container is or can be fixedly connected to the housing and the bracket having the opening means to be arranged on the housing such that it can rotate with respect to the housing, preferably by an angle between 5° and 360°, particularly preferably between 5° and 15° or between 180° and 360°, whereby the rotary motion of the bracket is limited, in particular through a limit stop and/or a snap-in locking device.

The invention can further provide attaching means for attaching the container to the bracket to be arranged on the bracket, in particular an internal thread, a bayonet closure or pegs forming a thread section.

Moreover, the invention can provide, while the bracket is in its basic position in the absence of a container, the thread or cam disk to fix the opening means in place and the gas cartridge to be closed and, while the bracket is in its rotated position having a container attached to it, the thread or cam disk fixes the opening means in place such that the compressed gas container is connected to an opening in the bracket in a gas-permeable manner.

Regarding reusable dispensing devices, the invention can provide that the compressed gas container is or can be connected in detachable manner to a fixation on the housing, in particular on the inside of the housing, preferably by means of a thread, particularly preferably an internal thread, on the fixation and a counter-thread, particularly preferably an external thread, on the compressed gas container.

The fixation and the housing can be made as a joint preform.

The invention can just as well provide the container to be opened during the insertion of the container into the dispensing device.

Moreover, the invention can provide the bracket to have an opening and a cylindrical tube arranged on it that merges into the opening and is supported like in a bearing such that it can be rotated about its axis or shifted along an axis with respect to the compressed gas container, whereby the bracket preferably is supported like in a bearing such that it can be rotated and/or shifted in a part of the housing that is provided as a sleeve.

The invention can just as well provide the bracket to have at least one sealing ring or sealing disc arranged on it that can be used to connect the container tightly to the bracket having the dispensing device.

The invention can provide the dispensing device to be made of plastic material, at least in part, preferably this will be the housing, the bracket, the tube, the opening means except for the hollow mandrel, the trigger, the handle, the cam disk, the thread and/or the fixation.

The object of the invention with respect to a method is met in that the force to be applied while inserting the container is utilised to rotate and/or shift the bracket, in that the rotating or shifting of the bracket moves opening means against a compressed gas container of the dispensing device and the compressed gas container is opened through the motion of the opening means.

In this context, it is preferable for the compressed gas container to be opened while the container is being attached to the dispensing device in a fixed or at least pressure-tight manner or after connecting the container to the dispensing device in a fixed or at least pressure-tight manner. This ensures that the pressure is not released prematurely even if the operating facility is opened in order to adjust the gas flow from the compressed gas container.

In this context, the invention can provide the gas flowing from the compressed gas container to be guided to the bracket and to apply a pressure onto at least a section of the container.

The pressure thus applied presses the container out when the container is opened in one place.

Moreover, the invention can provide the pressure to propel a feed plunger in the container, in particular in the cartridge or cartridge system, causing the content of the container to be expelled from the container.

The invention can just as well provide for the cross-section of a connection of the compressed gas container to the bracket, and thus a pressure acting on the container, to be adjusted by means of an operating facility, in particular a throttle valve.

In addition, the invention can provide the bracket to be rotated or shifted up to a limit stop or a snap-in locking means.

What this attains is that the strongly increasing resistance to insertion of the container due to the limit stop or the snap-in locking means indicates to the user inserting or rotating-in the container that the container is fully inserted, and/or that the dispensing device has been activated.

According to the invention, another procedural step can provide the opening means to be linearly shifted against the compressed gas container.

The object is also met through the use of an extruding device of this type, in particular while applying a method of this type, for extruding pasty one-component polymethylmethacrylate bone cements, pasty two-component polymethylmethacrylate bone cements, pasty three-component polymethylmethacrylate bone cements, dental impression materials, inorganic bone cements and/or polymethylmethacrylate bone cements, preferably through mixing a powder component and a liquid monomer component.

The invention is based on designing the dispensing device such that the user cannot open the compressed gas container, such as, for example, a compressed gas cartridge, before the cartridge or container is inserted into the dispensing device and such that the compressed gas container can be opened only with the cartridge or container inserted. It is particularly advantageous to have the compressed gas container open at the same time while the cartridge or container is being inserted into the dispensing device. It is thus basically impossible for compressed gas to be released from the compressed gas container due to premature actuation of the opening means without a cartridge or container being connected to the dispensing device. This prevents the compressed gas from being released inadvertently and the dispensing device being rendered unusable or inactive as a result.

For the reasons stated above, it is sensible that the coupling of the cartridge to the dispensing device during medical application of gas-driven dispensing devices proceeds at least synchronous to the gas cartridge being opened. This allows the gas cartridge to be prevented effectively from being opened inadvertently. Moreover, it is sensible that the gas cartridge can be opened no earlier than when the cartridge is fixed to the dispensing device in a mechanically safe manner.

The idea underlying the invention is also to utilise the mechanical process of connecting the cartridge or container to the dispensing device for opening the compressed gas container concurrently. This means, when the container is rotated or screwed-in by means of a thread or peg into the dispensing device and/or the applicator, the bracket and/or connecting means rotate(s) along at least several degrees, whereby said rotary motion is utilised to open the compressed gas container. Accordingly, the compressed gas container can be opened only while the container is being inserted into the dispensing device. If a snap-in locking means for attaching the cartridge or container is arranged on the dispensing device in place of a thread or peg, the force exerted during the insertion process is utilised to operate the opening means in order to open the gas cartridge. For this purpose, the pressure applied to the bracket to connect the cartridge or container to the dispensing device is converted into a motion of the opening means against the compressed gas container. In either case, the compressed gas container is protected from being opened prematurely and inadvertently and is opened through the force required for inserting the cartridge or container, i.e. the force applied while the container is being inserted or the torque applied while the container is being rotated or screwed into the bracket.

Figure 2:
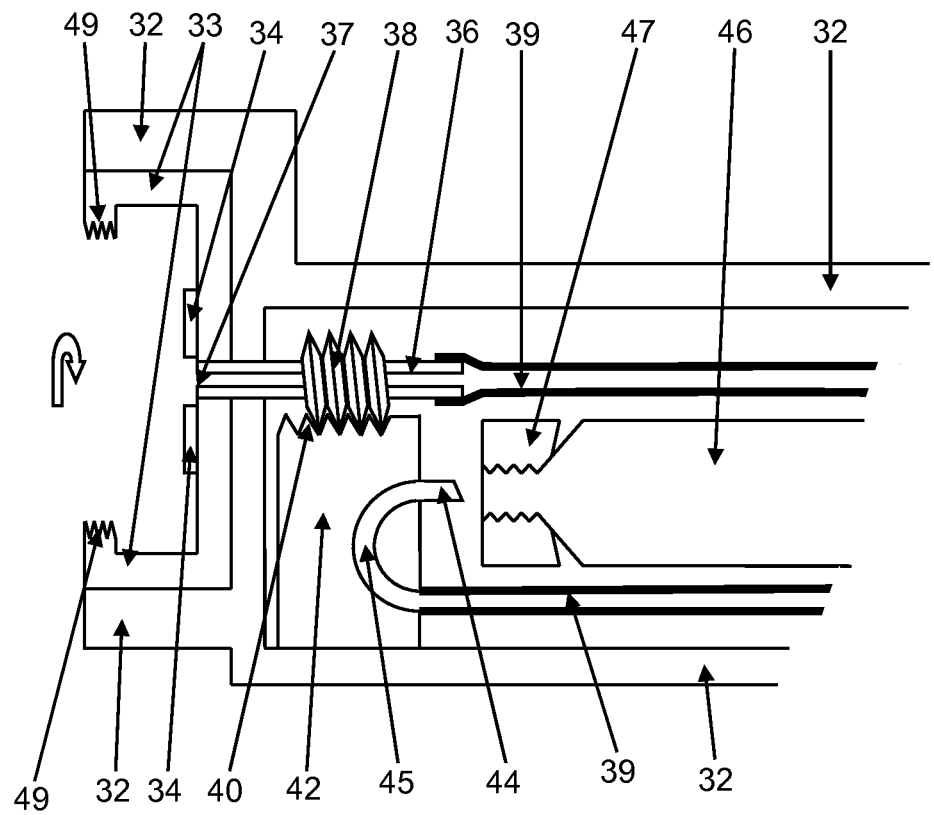
Figure 3:
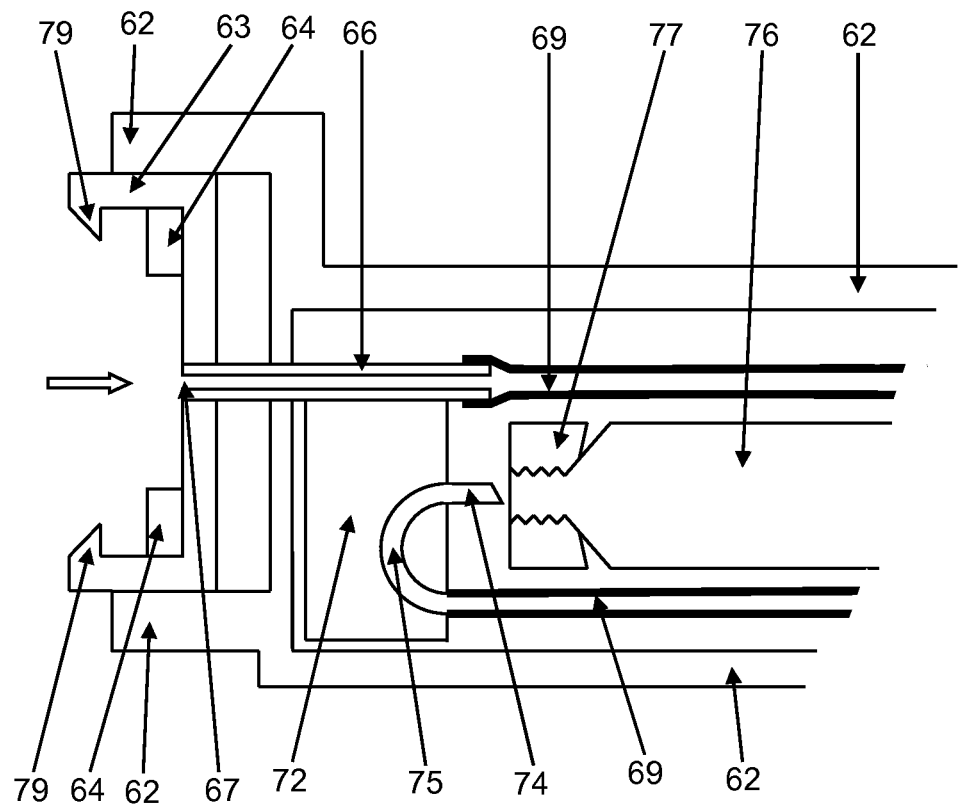

Exemplary embodiments of the invention shall be illustrated in the following on the basis of three schematic figures, though without limiting the scope of the invention. In the figures:

FIG. 1: shows a schematic cross-sectional view of a dispensing device according to the invention having a bracket that can be rotated;

FIG. 2: shows a schematic cross-sectional view of a front part of a second dispensing device according to the invention having a bracket that can be rotated; and FIG. 3: shows a schematic cross-sectional view of a front part of a third dispensing device according to the invention having a bracket that can be shifted.

FIG. 1 shows a schematic cross-sectional view of a dispensing device 1 according to the invention. The dispensing device 1 comprises a housing 2 which can, for example, be manufactured from plastic materials. A bracket 3 having a seal 4 is arranged in the front part of the housing 2. The bracket 3, and thus the seal 4 as well, are supported like in a bearing, such that they can rotate therein, in a sleeve that is formed by the housing 2 and takes up the bracket 3. The fact that the bracket 3 can be rotated is indicated through the open arrow. A cylindrical tube 6 is connected to the bracket 3 and merges into an opening 7 in the bracket 3. The opening 7 and the tube 6 connect the inside of the housing 2 to the sleeve formed through the housing 2 or to the front side of the bracket 3, as it may be. The tube 6 has a cam disk 8 attached to it that rotates along upon a rotation of the bracket 3, and thus of the tube 6, about the axis of the tube 6. Accordingly, the bracket 3 can be rotated about the axis formed through the tube 6. The tube 6 projects into the inside of the housing 2.

On the side opposite from the opening 7, the tube 6 is connected to a compressed gas conduit 9. The connection is sufficiently firm such that the compressed gas conduit 9 does not detach from the tube 6 upon the action of a gas pressure. This applies to all connections of the compressed gas conduit 9 to other components of the dispensing device 1. The compressed gas conduit 9 has a throttle valve 10 arranged in it that can be adjusted by means of a trigger 11. The throttle valve 10 can be used to adjust the cross-section of the connection formed through the compressed gas conduit 9. The compressed gas conduit 9 is also attached to opening means 12 having a hollow mandrel 14 and forms, through a feed-through 15 in the opening means 12, another pressure-resistant connection to the compressed gas conduit 9. The opening means 12 is arranged in the housing 2 of the dispensing device 1 such that it can be shifted in the direction of the hollow mandrel 14. In this context, the opening means 12 is arranged below the cam disk 8 of the tube 6 in such manner that the cam disk 8 engages a counterpart of the opening means 12 (indicated through the bevel at the left upper end of the opening means 12) when the bracket 3, and thus the cam disk 8, rotates. This shifts the opening means 12 to the right in FIG. 1 when the bracket 3 rotates. In order to ensure the mobility of the opening means 12, the compressed gas conduit 9 connected to the opening means 12 is a flexible tube or a bellows, at least over regions thereof.

A gas cartridge 16, as compressed gas container, is attached to the right and next to the opening means 12 in a fixation 17 on the housing 2. The gas cartridge 16 is to be screwed into the fixation 17. For this purpose, the gas cartridge 16 is provided with an external thread and an internal thread is provided in the fixation 17. The right lower part of the housing 2 forms a gun handle 18 on which the dispensing device 1 can be held such that the trigger 11 can be operated easily even upon one-handed operation.

Pegs 19 are provided on the bracket 3 and form a thread section. A container (not shown), for example a cartridge or a cartridge system for a medical cement, can be screwed into said thread section.

When a container is being attached to the bracket 3, i.e. rotated or screwed-in, the container can be rotated in up to the seal 4. Subsequently, the container is arrested at the bracket 3. Rotating the container further, the bracket 3, and thus the tube 6 having the cam disk 8, is made to rotate in the housing 2. The cam disk 8 presses with its bevelled edge onto the bevelled edge of the counterpart on the opening means 12. This pushes the opening means 12 towards the gas cartridge 16. The hollow mandrel 14 penetrates into the gas cartridge 16 and thus opens it.

The gas from the gas cartridge 16 can flow through the hollow mandrel 14, the feed-through 15, the compressed gas conduit 9, and the throttle valve 10 into the tube 6. Ultimately, the gas flows from the gas cartridge 16 through the opening 7 to a section of the screwed-in container. Since said section of the container is sealed through the seal 4, a gas pressure can build up therein and act on the container. The pressure of the gas acting on said section of the container extrudes a material that is contained in the container from the container. The extrusion rate can be adjusted through adjusting the throttle valve 10 via the trigger 11.

Accordingly, the gas cartridge 16 is opened only when the container is fully secured to the dispensing device 1. Since the bracket 3 cannot be rotated easily without container inserted, incorrect operation of the dispensing device 1 according to the invention, i.e. premature opening of the gas cartridge 16, is all but excluded.

FIG. 2 shows a schematic cross-sectional view of a front part of an alternative dispensing device. This device also comprises a housing 32, in which a bracket 33 for a container (not shown) is supported like in a bearing such that it can be rotated. A seal 34 is arranged in the bracket 33 and has a flat front side of an inserted container touch against it in order to produce a gas-tight connection of the container to the bracket 33. The bracket 33 has a tube 36 arranged on it that extends an opening 37 into the bracket 33. A thread 38 is provided about the tube 36. Unlike all other components of the dispensing device, the thread 38 is shown in FIG. 2 not as in a cross-section, but rather in a schematic side view, i.e. top view. The tube 36 connects the opening 37 in the bracket 33 to a compressed gas conduit 39. A valve (not shown) for controlling a gas flow is provided in the compressed gas conduit 39.

The thread 38 of the tube 36 engages a counter-thread 40, which is part of opening means 42, and is arranged below the thread 38 such as to be shiftable in the housing 32. One side of the opening means 42 has a hollow mandrel 44 provided on it that is connected to the compressed gas conduit 39 through a feed-through 45 in the opening means 42. The feed-through 45 is arced in a curve in the opening means 42 at which a gas flow can be deflected. The purpose of the hollow mandrel 44 is to open a gas cartridge 46 when the opening means 42 shifts towards the gas cartridge 46 as a result of the bracket 33, and thus the thread 38, rotating. While the opening means 42 can be shifted in the housing 32 in longitudinal direction of the gas cartridge 46, the gas cartridge 46 itself is firmly connected to the housing 32 through a fixation 47. The gas cartridge 46 can be connected to the fixation 47, and thus to the housing 32, through a snap-in locking means that engages a counter-snap-in locking means on the fixation 47.

The bracket 33 has attaching means in the form of an internal thread 49 provided on it into which a container having a corresponding external thread can be screwed. As soon as the container is screwed into the attachment thread 49 up to the limit stop, rotating the container further effects a rotation of the bracket 33 and thus of the tube 36. The thread 38 on the tube 36 on the inside of the housing 32 rotates along with the tube 36. The thread 38 engages the counter-thread 40 of the opening means 42. Rotating the thread 38 pushes the opening means 42 towards the gas cartridge 46. The hollow mandrel 44 penetrates into the head of the gas cartridge 46 and thus opens the cartridge. The compressed gas is guided from the gas cartridge 46 through the hollow mandrel 44 through the feed-through 45 into the compressed gas conduit 39. From there, the gas is guided further through the tube 36 to the opening 37.

The pressure existing at the opening 37 of the bracket 33 acts on the container and is utilised to extrude the container content. The cylindrical bracket 33 having a circular base area sits firmly fitted in the cylindrical sleeve formed through the housing 32. With the exception of the thread 49, the cylindrical bracket 33 is rotationally symmetrical, whereby the tube 36 extends symmetrically along the axis of symmetry.

Accordingly, the rotation of the bracket 33 and tube 36 proceeds about the axis of symmetry of the cylindrical tube 36 (the direction of rotation is indicated through the open arrow). Due to its firm fit in the housing 32, the bracket 33 cannot be rotated easily. However, the container to be screwed in is a suitable tool for rotating the bracket 33 in the housing 32 since a sufficient force can be transmitted to the bracket 33 by means of the container in order to overcome the static friction of the firm fit. This ensures that a rotation of the bracket 33 with respect to the housing 32 can proceed only with a container inserted. Since the opening means 42, being a shiftable body having the hollow mandrel 44 and a feed-through 45 connected to the hollow mandrel 44, can be moved only by means of propelling via the thread 38 on the tube 36 of the bracket 33, the hollow mandrel 44 can be punctured into the gas cartridge 46 only with a container inserted. Accordingly, the compressed gas container 46 and/or the gas cartridge 46 can also be opened only if a container has been inserted into the dispensing device.

It applies to both exemplary embodiments shown in FIGS. 1 and 2 that the torque transmitted to the bracket 3, 33 through the rotation of the fixed container is transmitted through the cam disk 8 or the thread 38 and the counter-means 40 on the opening means 12, 42 to the opening means 12, 42, respectively, and is converted into a linear motion of the opening means 12, 42 with respect to the compressed gas container 16, 46 through the geometry of the arrangement (the shapes of the cam disk 8 and counter-cam disk as well as of the thread 38 and counter-thread 40). The force of said motion of the opening means 12, 42 is utilised to open the compressed gas container 16, 46. In this context, suitable selection of the inclination of the edge of the cam disk 8 or thread 38 allows a desired amplification of the force transmission to be attained, i.e. the gear thus formed can be adjusted.

FIG. 3 shows a schematic cross-sectional view of a front part of an another dispensing device according to the invention. In this embodiment, a housing 62 has a bracket 63 for a container, such as, for example, a cartridge or a cartridge system, arranged in it that can be shifted in it. To insert the cartridge or container into the bracket 63, the cartridge or container are plugged-in in the direction of the open arrow. A seal 64 is arranged in the bracket 63 about the connection to a tube 66. The tube 66 merges into an opening 67 in the bracket 63. The tube 66 is connected to a compressed gas conduit 69. The compressed gas conduit 69 has a valve (not shown) for regulating the free cross-section of the compressed gas conduit 69 arranged in it.

Opening means 72 are fixedly connected to the tube 66. The opening means 72 comprise a hollow mandrel 74 that is connected to the compressed gas conduit 69 through a passageway 75. Shifting the bracket 63 in the direction of the open arrow also shifts the tube 66, and thus the opening means 72 connected to the tube 66. The hollow mandrel 74 is pushed into a compressed gas container 76 during this motion which opens the compressed gas container 76. The compressed gas container 76 is attached by means of a thread on a fixation 77 that is fixedly connected to the housing 62. In order to keep the container in the bracket 63, snap-in locking means 79 are provided on the bracket 63 and engage counter-snap-in locking means on the container. Accordingly, the container is connected to the dispensing device simply by pressing it into the bracket 63.

The pressure applied to the bracket 63 during insertion of the container shifts the bracket 63 in the housing 62 of the dispensing device in the direction of the open arrow. This pushes the tube 66 deeper into the inside of the housing 62. This shifts the opening means 72 towards the compressed gas container 76. The hollow mandrel 74 penetrates into a weakened site provided for this purpose on the head of the compressed gas container 76, and open the same. The pressure from the compressed gas container 76 is guided through the hollow mandrel 74, the feed-through 75, the compressed gas conduits 69, and the tube 66 to the container attached in the bracket 63. The pressure can be utilised to extrude the container content.

The features of the invention disclosed in the preceding description and in the claims, figures, and exemplary embodiments, can be essential for the implementation of the various embodiments of the invention both alone and in any combination.

LIST OF REFERENCE NUMBERS

1 Dispensing device
2, 32, 62 Housing
3, 33, 63 Bracket
4, 34, 64 Seal
6, 36, 66 Tube
7, 37, 67 Opening
8 Cam disk
9, 39, 69 Conduit
10 Throttle valve
11 Trigger
12, 42, 72 Opening means
14, 44, 74 Hollow mandrel
15, 45, 75 Feed-through
16, 46, 76 Gas cartridge
17, 47, 77 Fixation
18 Handle
19 Pegs
38 Thread
40 Counter thread
49 Thread
79 Snap-in locking means

The invention claimed is:

1. A dispensing device for extruding a content of a first container through applying a compressed gas, the device comprising a housing, at least one compressed gas container, an operating facility, and an opener, wherein the opener is mobile with respect to the at least one compressed gas container wherein the dispensing device further comprises a bracket, wherein the bracket and the opener are in operative connection for opening the at least one compressed container by movement of the bracket relative to the compressed gas container when the first container is attached to the bracket, wherein the first container is a cartridge or a cartridge system having multiple cartridges, wherein the cartridge or the cartridge system contains a bone cement or a multi-component bone cement.

2. The dispensing device according to claim 1, wherein the at least one compressed gas container comprises at least one gas cartridge, wherein at least one of the gas cartridges is openable with the opener and the opener is shiftable in a longitudinal direction of the at least one gas cartridge.

3. The dispensing device according to claim 1, wherein the cartridge or the cartridge system has at least one feed plunger arranged therein that is mobile therein and is drivable by means of gas pressure from the least one compressed gas container.

4. The dispensing device according to claim 1, wherein the at least one compressed gas container is connected through at least one compressed gas conduit to an opening in the bracket, wherein the operating facility is arranged in a connection established through the at least one compressed gas conduit.

5. The dispensing device according to claim 4, wherein the at least one compressed gas conduit comprises at least one piece of hose or is or is made of at least one flexible hose.

6. The dispensing device according to claim 1, wherein the operating facility comprises an adjustable throttle valve that is operable by means of a trigger.

7. The dispensing device according to claim 1, wherein the dispensing device further comprises a handle on which a trigger for operating the operating facility is arranged.

8. The dispensing device according to claim 1, wherein the opener comprises a hollow mandrel that is usable to puncture, and thus open, the compressed gas container, wherein a pressure-tight connection to the compressed gas container can be established through the hollow mandrel and the hollow mandrel is connected to at least one compressed gas conduit.

9. The dispensing device according to claim 1, wherein the bracket is arranged such as to be mobile with respect to the at least one compressed gas container and the opener is to be connected fixedly to the bracket, wherein the first container is insertable into the bracket and the bracket comprises snap-in locking means that engage opposite snap-in locking means on the first container, and further wherein the at least one compressed gas container can be opened through force acting on the bracket when the first container is being attached in the bracket of the dispensing device.

10. The dispensing device according to claim 9, wherein the at least one compressed gas container is fixedly connected to the housing and the bracket having the opener is arranged on the housing such as to be linearly mobile with respect to the housing.

11. The dispensing device according to claim 1, wherein the first container can be rotated or screwed into the bracket and the bracket is arranged such that it is rotatable with respect to the opener, wherein a portion of the bracket extending into an inside of the housing has a thread, which is interlocked with the opener, arranged on the portion or a cam disk engaging a counter-part on the opener arranged on the portion, and the opener are arranged such as to be linearly mobile with respect to the bracket and the at least one compressed gas container such that a rotation of the bracket upon the first container being attached to the bracket leads to a linear motion of the opener with respect to the at least one compressed gas container and thus to the at least one compressed gas container being opened.

12. The dispensing device according to claim 11, wherein the at least one compressed gas container is fixedly connectable to the housing and the bracket having the opener is arranged on the housing such that it is rotatable rotate with respect to the housing by an angle between 5° and 360°, wherein the rotary motion of the bracket is limited through a limit stop or a snap-in locking device.

13. The dispensing device according to claim 11, wherein attaching means for attaching the first container to the bracket are arranged on the bracket, wherein the attaching means comprises an internal thread, a bayonet closure or pegs forming a thread section.

14. The dispensing device according to claim 11, wherein, while the bracket is in a first position in the absence of the first container, the thread or cam disk fixes the opener in place and the compressed gas container is closed and, while the bracket is in a rotated second position having the first container attached to thereto, the thread or cam disk fixes the opener in place such that the at least one compressed gas container is connected to an opening in the bracket in a gas-permeable manner.

15. The dispensing device according to claim 1, wherein the at least one compressed gas container is connected in detachable manner to a fixation on the housing, by means of a thread on the fixation and a counter-thread on the at least one compressed gas container.

16. The dispensing device according to claim 1, wherein the at least one compressed gas container is openable during insertion of the first container into the dispensing device.

17. The dispensing device according to claim 1, wherein the bracket has an opening and a cylindrical tube arranged on the bracket that merges into the opening and is supported such that the bracket is rotatable about its axis or shifted along an axis with respect to the at least one compressed gas container, wherein the bracket is supported such that the bracket is rotatable or shiftable in a part of the housing that is provided as a sleeve.

18. The dispensing device according to claim 1, wherein the bracket has at least one sealing ring or sealing disc arranged thereon that is usable to connect the first container tightly to the bracket.

19. A method for activating a dispensing device for extruding a content of a first container through applying a compressed gas, wherein the device comprises a housing, at least one compressed gas container, an operating facility, and an opener, wherein the opener is mobile with respect to the at least one compressed gas container, wherein the dispensing device further comprises a bracket for attaching the first container to the dispensing device, wherein the bracket and the opener are in operative connection for opening the at least one compressed gas container by movement of the bracket relative to the compressed gas container when the first container is attached to the bracket, the method comprising:
   inserting the container containing a material to be extruded into the bracket of the dispensing device, wherein force applied while inserting the first container is utilized to rotate or shift the bracket, wherein the rotating or shifting of the bracket moves the opener against the at least one compressed gas container of the dispensing device, and the at least one compressed gas container is opened through motion of the opener.

20. The method according to claim 19, further comprising:
   guiding the gas flowing from the at least one compressed gas container to the bracket; and
   applying a pressure onto at least a section of the first container.

21. The method according to claim 20, wherein the pressure propels a feed plunger in the first container causing a content of the first container to be expelled from the first container.

22. The method according to claim 19, wherein a cross-section of a connection of the first container to the bracket, and thus a pressure acting on the first container, is adjusted by means of the operating facility or a throttle valve of the operating facility.

23. The method according to claim 19, wherein the bracket is rotated or shifted up to a limit stop or a snap-in locking means.

24. The method according to claim 19, wherein the opener is shifted linearly against the at least one compressed gas container.

25. The method according to claim 19, further comprising:
   mixing a powder component and a liquid monomer component for extruding a pasty one-component polymethylmethacrylate bone cement, a pasty two-component polymethylmethacrylate bone cement, a pasty three-component polymethylmethacrylate bone cement, a dental impression material materials, an inorganic bone cement or a polymethylmethacrylate bone cement.

26. A dispensing device for extruding a content of a first container through applying a compressed gas, the device comprising:
- a housing having an interior;
- at least one compressed gas container having an entire length defined between a first end and a second end located opposite with respect to the first end of the at least one compressed gas container;
- an operating facility comprising at least one selected from a trigger and a valve;
- an opener that is mobile with respect to the at least one compressed gas container; and
- a bracket;
- wherein the bracket and the opener are in operative connection for opening the at least one compressed gas container by movement of the bracket relative to the compressed gas container when the first container is attached to the bracket, and
- further wherein the entire length of the at least one compressed gas container is located or positioned within the interior of the housing.

* * * * *